United States Patent [19]
Hashimoto et al.

[11] Patent Number: 5,961,886
[45] Date of Patent: Oct. 5, 1999

[54] CUT FLOWER PRESERVATIVE SLURRY COMPOSITION

[75] Inventors: Masaki Hashimoto, Ibaraki; Takaharu Tanaka, Osaka, both of Japan

[73] Assignee: Suntory Limited, Osaka, Japan

[21] Appl. No.: 08/634,722

[22] Filed: Apr. 19, 1996

[30] Foreign Application Priority Data

Apr. 20, 1995 [JP] Japan .................................. 7-095537

[51] Int. Cl.$^6$ .................................................. C09K 15/32
[52] U.S. Cl. .................................. 252/400.3; 252/400.23; 252/382; 252/383; 504/114; 504/115
[58] Field of Search ........................... 252/400.3, 400.23, 252/382, 383; 504/114, 115

[56] References Cited

U.S. PATENT DOCUMENTS

| | | | |
|---|---|---|---|
| 4,092,145 | 5/1978 | Willard, Sr. | 71/68 |
| 4,238,374 | 12/1980 | Durham et al. | 47/41.4 |
| 4,985,061 | 1/1991 | Hughes | 71/68 |
| 5,180,585 | 1/1993 | Jacobson et al. | 424/405 |
| 5,284,818 | 2/1994 | Shafer et al. | 504/115 |
| 5,350,735 | 9/1994 | Kimnnersly et al. | 504/147 |
| 5,472,972 | 12/1995 | Ohkouchi et al. | 514/373 |
| 5,580,840 | 12/1996 | Harms et al. | 504/115 |
| 5,747,416 | 5/1998 | McArdle | 504/115 |

FOREIGN PATENT DOCUMENTS

| | | |
|---|---|---|
| 0 270 129 | 6/1988 | European Pat. Off. . |
| 03 106 801 | 5/1991 | Japan . |
| 04 120 001 | 4/1992 | Japan . |
| 6 263 612 | 9/1994 | Japan . |
| 6-279202 | 10/1994 | Japan . |
| 06 279 202 | 10/1994 | Japan . |

*Primary Examiner*—C. H. Kelly
*Attorney, Agent, or Firm*—Burns, Doane, Swecker & Mathis, L.L.P.

[57] ABSTRACT

A cut flower preservative slurry composition comprising a water insoluble or hardly soluble cut flower preservative component and a dispersing agent for dispersing the preservative component in water to form a slurry.

34 Claims, No Drawings

CUT FLOWER PRESERVATIVE SLURRY COMPOSITION

BACKGROUND OF THE INVENTION

1. Field of the Invention

The present invention relates to a cut flower preservative slurry composition.

2. Description of the Related Art

Cut flowers generally start to lose their freshness immediately after they are harvested. With each passing day, their petals and leaves wilt and yellow until finally the aesthetic value of the flowers is lost. The most important problems to be solved in the cut flower business, which is expected to increase the demand in the future, are how to prevent the loss of freshness of the cut flowers.

In the past, for this purpose, two types of cut flower preservative have been used: liquid type in which a high concentration liquid containing the cut flower preservative component is diluted with water when applied and solid type comprising a powdered, granular, or tableted preservative, which are dissolved in a predetermined amount of water when applied. These two types preservative, however, not only require troublesome work such as adjustment of the concentration or stirring, but also, since they are used to be homogeneous solutions, had the preservative component distributed throughout the container, which is not efficient. Further, there is the risk of environmental pollution upon its disposal. Some types of preservative component should be treated by a neutralizing agent etc.

On the other hand, it has been suggested to use antibacterial zeolite, which expects a cleansing action due to its antibacterial effect, as a preservative component for cut flower preservative (Japanese Unexamined Patent Publication (Kokai) No. 63-265809 or Japanese Examined Patent Publication (Kokoku) No. 4-28646). The above-mentioned antibacterial zeolite, however, is a fine powder having an average particle size of generally about 0.6 to 2.0 $\mu$m, and therefore, when handled gives off fine particulates which adhere to the surrounding devices or the body due to static electricity etc.

Further, reports have been made of tablet type cut flower preservative obtained by adding equivalent amounts of weak acids or alkali carbonates to inorganic antibacterial agents such as apatite, zeolite, and phosphate salts carrying antibacterial metals, tableting them to make so-called foaming tablets, and using carbon dioxide gas to cause the inorganic antibacterial agents etc. to disperse in the container as a whole (Japanese Unexamined Patent Publication (Kokai) No. 6-279202). However, the method for dispersing the component by carbon dioxide gas etc. suffers from the problems that the component is not always broken down into the desired particle size, the generation of carbon dioxide gas requires mixture of at least two components, the economicalness is decreased including the use of the tableting process etc., there is a risk of harm to the cut flowers or salt pollution in the wastewater depending on the amount and type of the components for producing the carbon dioxide gas, the foaming tablets are inherently extremely hygroscopic, a reaction is easily caused even with the moisture in the air and the water which is produced from the reaction further causes the reaction to proceed until the tablet is destroyed, etc. Thus, it has been necessary to take special measures with regard to hygroscopic packaging, addition of desiccants, etc.

SUMMARY OF THE INVENTION

Accordingly, in view of the finding the facts that cut flowers absorb water only from their cuts, the object of the present invention is to create a cut flower preservative which is efficient and economical, superior in the effect of preserving the freshness of the cut flowers, safe to the environment, and free from the need of complicated work or special caution.

In accordance with the present invention, there is provided a slurry-like cut flower preservative composition characterized by causing a water insoluble or hardly soluble cut flower preservative component to disperse in water together with a dispersing agent to make a slurry.

DETAILED DESCRIPTION OF PREFERRED EMBODIMENTS

After having the intensive research, the present inventors found that by using a water insoluble or hardly soluble cut flower preservative component and making this disperse in water together with a dispersing agent to make a slurry, it was possible to obtain a cut flower preservative composition which solved the above problems, and thereby completed the present invention.

Since the cut flower preservative composition of the present invention is in a slurry state, it is free of the defects derived from a fine powder as described above before the addition into water, is simple to handle, and does not require any troublesome adjustment of the concentration of the solution or stirring. Also, after being poured into water, the preservative component immediately precipitates and deposits as its original powder and is efficiently absorbed from the cuts in the cut flowers, and therefore, is effective even in small amounts. Further, since the preservative component according to the present invention is insoluble or hardly soluble in water, there is no fear of environmental pollution due to the wastewater. Furthermore, since the cut flower preservative composition of the present invention is in a slurry state, the problems of a fine powder in handling the water insoluble or hardly soluble cut flower preservative component are solved at all of the stages of manufacture and use.

Examples of the water insoluble or hardly soluble cut flower preservative component used in the present invention are those having an action for preserving the freshness of cut flowers due to a water uptake effect, effect of suppressing plant aging, nutritional effect, ethylene suppressing effect, plant growth control effect, bactericidal effect, antiseptic effect, etc. or their synergistic effects. Examples of such preservative components are antibacterial metal (for example, silver, copper, and zinc)-carrying apatite, zeolite (hereinafter zeolite in which some cations thereof are replaced with silver ions is referred to as silver-zeolite), phosphate salts, silica, alumina, activated carbon, insoluble inorganic silver compounds such as silver oxide and silver chloride, insoluble organic ethylene inhibitors such as aminoisobutyric acid, and insoluble organic antibacterials such as thiabendazole and tetrachloroisophthalonitrile. In addition to these, any chemical exhibiting effective action in preserving the freshness of cut flowers may be used in the present invention.

Note that among these water insoluble or hardly soluble cut flower preservative components, silver-zeolite is preferable. Further, the content of silver in the silver-zeolite is preferably at least 2.5% by weight, more preferably 5 to 20% by weight, from the viewpoint of the effect for preserving the freshness of the cut flowers.

The water insoluble or hardly soluble cut flower preservative component usable in the present invention is preferably in the form of powder. From the viewpoints of the efficiency of absorption at the cut surface, the water uptake of the cut flowers, the effect of preservation of freshness, and the dispersion and fluidity as a slurry, it is preferable if it is a fine powder having an average particle size of not more than 5 µm, more preferably not more than 2 µm.

The dispersing agent usable for making a slurry of the preservative component in the present invention is not particularly limited so long as a fluid slurry of the water insoluble or hardly soluble cut flower preservative component is formed, and the dispersing agent is superior in sustainability of the dispersion and is free from precipitation or separation even after long-term storage. Further, it is preferable if the cut flower preservative component quickly precipitates and deposits uniformly on the bottom of the container after being poured into water. Examples of such dispersing agent are cationic, anionic, and nonionic surfactants, thickeners such as xanthan gum, phosphates, and polymer type dispersants, preferably an alkylamine based nonionic surfactant such as a polyoxyethylene alkylamine based surfactant, an ester based nonionic surfactant such as a polyoxyethylene hydrogenated castor oil triisostearate and a polyethylene glycol diisostearate and an ether based nonionic surfactant such as a polyoxyethylene hydrogenated castor oil, more preferably nonionic type polyoxyethylene alkylamine based surfactants. Further, if desired, it is also possible to add fluidizing agents and dispersion stabilization agents such as polyacrylamide and humectants such as sorbitol, polyethylene glycol, 1,3-butylene glycol and concentrated glycerin.

The contents of the components in the cut flower preservative slurry composition according to the present invention are not particularly limited, but the water insoluble or hardly soluble cut flower preservative component is preferably contained in an amount of 5 to 70% by weight, more preferably 30 to 60% by weight, based on the total weight of the slurry. Further, the dispersing agent is preferably included in an amount of 0.05 to 10% by weight, more preferably 0.1 to 5% by weight based on the total weight of the slurry. Furthermore, if desired, the fluidizing agent, the dispersion stabilization agent or the humectants is preferably included in an amount of less than 10% by weight, more preferably 0.1 to 5% by weight based on the total weight of the slurry. The balance is water. In addition, any other additives (such as nutrients such as glucose and starch and fertilizer components including nitrate, phosphate, and potassium) generally used in the past may be compounded therein.

The cut flower preservative slurry composition according to the present invention can be used as either a pretreatment agent or a post-treatment agent or can be used continuously from pretreatment to post-treatment.

EXAMPLES

The cut flower preservative composition of the present invention will now be explained in detail by the following Examples, but these Examples, of course, do not limit the present invention in any way.

Example 1: Preparation of Slurry

One gram of the dispersing agent polyoxyethylene oleylamine (E.O.=2) (Esomin O-12 (made by Lion Corporation)) was added to 1 liter of deionized water which was then stirred at 20° C. for 10 minutes. After confirming homogeneous, 500 g of the cut flower preservative component, that is, silver-zeolite (containing 5 wt % of silver) was gradually added while stirring and made to disperse. After mixing, the mixture was further stirred slowly at 20° C. for 1 hour to make a slurry.

Test Example 1: Test of Stability of Dispersion of Slurry

The stability of dispersion of the slurry prepared in Example 1 after the elapse of a certain time was measured. The method of measurement was to pour the slurry into a transparent covered container (50 ml). The height immediately after pouring was used as 100%. The height of the transparent supernatant on the dispersion was measured and the precipitation behavior was expressed as a "% dispersion". According, a "100% dispersion" means that no supernatant layer was formed. As a result, the composition remained a 100% dispersion even after the elapse of 120 days. Thus, a good stability of the dispersion was observed.

Next, the long term dispersion stability was tested by a freezing and thawing test used to measure long term (2 to 3 year) dispersion stability. The slurry prepared in Example 1 was poured into the same container as mentioned above, allowed to stand at −9° C. for 14 hours, followed by 23° C. for 10 hours, and was measured as for the % dispersion. Further, the consistency of the precipitate formed in the container after the standing was investigated by contact with a spatula. The precipitates were judged by the presence of formation of precipitate and the degree thereof and the ease, difficulty, or impossibility of restirring the precipitate. The results were evaluated as follows:

A=No precipitate in dispersion

B=Formation of precipitate having soft consistency and easy to stir.

C=Formation of precipitate having medium degree of consistency and difficult to stir.

D=Formation of precipitate having hard consistency and impossible to stir.

Further, the same procedure test was repeated three days continuously. The results are shown in Table 1.

TABLE 1

| Results of Freezing and Thawing Test | | |
|---|---|---|
| No. of days elapsed | % dispersion | Consistency of precipitate |
| 1 | 95% | A |
| 2 | 93% | A |
| 3 | 90% | B |

Test Example 2: Test of Cut Flowers Preservation

Roses (Röte Rose) were cut into lengths of 50 cm within 2 hours after harvesting and the bottom leaves were stripped off. Twenty roses each per group were prepared. About 600 mg of the slurry prepared in Example 1 was added to 2 liters of tap water for the treatment group. Twenty roses were placed in each treatment group and treated at 7° C. for 24 hours. After treatment, the flowers were transferred to 2 liters of tap water, then were observed at 22° C. and their aesthetic value, weight, and bent neck rate were investigated. During the investigation, the water was not replaced, just supplemented. A similar procedure was performed for a comparison using just 2 liters of tap water for the untreated group.

The results of the test are shown in Table 2.

In Table 2, the average number of aesthetic days is the average of the number of days until each aesthetic value is lost, this value being judged by standards of bent neck, wilting, dryness, exposure of flower center, normal end of blooming, etc. The bent neck rate is the ratio of the number of flowers losing aesthetic value due to a bent neck. Further, the cumulative weight index is the cumulative value of the change in weight each day until the average number of aesthetic days indexed to the weight of the flowers at the start of the test being used as 100 of the value. The larger this value, the larger the increase in weight during viewing and the healthier the blooming.

TABLE 2

Results of Test on Effect of Preserving Freshness of Cut Flowers

| Group | Average aesthetic days | Bent neck rate | Cumulative weight index |
|---|---|---|---|
| Untreated | 8.4 days | 90% | 47 |
| Treated | 14.0 days | 5% | 137 |

Example 2: Preparation of Slurry

A 0.75 g amount of polyoxyethylene hydrogenated castor oil triisostearate (E.O.=30), 1.51 g of polyethylene glycol diisostearate (E.O.=6), 1.06 g of polyoxyethylene oleylamine (E.O.=2) (Esomin O-12 (made by Lion Corporation)) and 7.54 g of 1,3-butylene glycol were sufficiently stirred to give a mixture. The mixture was added to 1 liter of distilled water which was then stirred at 20° C. for 10 minutes. 500 g of the cut flower preservative component, that is, silver-zeolite (containing 10 wt % of silver) was added to the mixture which was then stirred at 20° C. for 30 minutes to form a slurry.

Example 3: Preparation of Slurry

One gram of the dispersing agent, polyoxyethylene oleylamine (E.O.=2) (Esomin O-12 (made by Lion Corporation)) was added to 1 liter of distilled water which was then stirred at 24° C. until the solution became homogeneous. The obtained solution was added at once to 500 g of the cut flower preservative component, that is, silver-zeolite (containing 20 wt % of silver) which had been stirring slowly, followed by stirring slowly at 24° C. for 1 hour to form a slurry.

As explained above, by using the cut flower preservative slurry composition according to the present invention, it is possible to preserve the freshness of cut flowers more efficiently and economically than a conventional cut flower preservative. Also, no complicated adjustment procedures are required, there is no trouble caused by a powder, and cut flowers can be preserved in freshness in a manner safe to both human health and the environment.

We claim:

1. A method for making a cut flower preservative composition comprising:
    adding into water a cut flower preservative slurry composition comprising a water insoluble or hardly soluble cut flower preservative component which is selected from the group consisting of a silver, copper or zinc-carrying apatite, zeolite, phosphate salts, silica, alumina, and activated carbon, insoluble inorganic silver compounds, insoluble organic ethylene inhibitors, and insoluble organic antibacterials and a dispersing agent for dispersing the preservative component in water.

2. A method as claimed in claim 1, wherein the cut flower preservative component is silver-zeolite containing at least 2.5% by weight of silver.

3. A method as claimed in claim 1, wherein the dispersing agent is an alkylamine based nonionic surfactant.

4. A method as claimed in claim 1, wherein the dispersing agent is selected from the group consisting of cationic, anionic, and nonionic surfactants; thickeners; phosphates; polymer type dispersants; an ester based nonionic surfactant; and an ether based nonionic surfactant.

5. A method as claimed in claim 1, wherein the insoluble inorganic silver compound comprises silver oxide or silver chloride.

6. A method as claimed in claim 1, wherein the insoluble organic ethylene inhibitor comprises aminoisobutyric acid.

7. A method as claimed in claim 1 wherein the insoluble organic antibacterials comprises thiabendazole or tetrachloroisophthalonitrile.

8. A method as claimed in claim 4, wherein the thickener is xanthan gum.

9. A method as claimed in claim 4, wherein the polymer type dispersant comprises an alkylamine based nonionic surfactant.

10. A method as claimed in claim 9, wherein the alkylamine based nonionic surfactant is a polyoxyethylene alkylamine based surfactant.

11. A method as claimed in claim 4, wherein the ester based nonionic, surfactant comprises a polyoxyethylene hydrogenated castor oil triisostearate or a polyethylene glycol, diisostearate.

12. A method as claimed in claim 4, wherein the ether based nonionic surfactant is a polyoxyethylene hydrogenated castor oil.

13. A method as claimed in claim 4, wherein the ether based nonionic surfactant is a nonionic type polyoxyethylene alkylamine based surfactant.

14. A method as claimed in claim 1, wherein the composition further comprises a fluidizing agent and/or a dispersion stabilization agent and/or humectants.

15. A method as claimed in claim 14, wherein the fluidizing agent and/or the dispersion stabilization agent is selected from the group consisting of polyacrylamides.

16. A method as claimed in claim 14, wherein the humectants are selected from the group consisting of sorbitol, polyethylene glycol, 1,3-butylene glycol and concentrated glycerin.

17. A method as claimed in claim 4, wherein the ether based nonionic surfactant is polyoxyethylene hydrogenated castor oil.

18. A method for preserving a cut flower comprising:
    adding into water a cut flower preservative slurry composition comprising a water insoluble or hardly soluble cut flower preservative component, which is selected from the group consisting of a silver, copper or zinc-carrying apatite, zeolite, phosphate salts, silica, alumina, and activated carbon, insoluble inorganic silver compounds, insoluble organic ethylene inhibitors, and insoluble organic antibacterial, and a dispersing agent for dispersing the preservative component in water, wherein a cut flower is present in said water or a cut flower is added to said water.

19. A method as claimed in claim 18, wherein the cut flower preservative component is silver-zeolite containing at least 2.5% by weight of silver.

20. A method as claimed in claim 18, wherein the dispersing agent is an alkylamine based nonionic surfactant.

21. A method as claimed in claim 18, wherein the dispersing agent is selected from the group consisting of cationic, anionic, and nonionic surfactants; thickeners; phosphates; polymer type dispersants; an ester based nonionic surfactant; and an ether based nonionic surfactant.

22. A method as claimed in claim 18, wherein the insoluble inorganic silver compound comprises silver oxide or silver chloride.

23. A method as claimed in claim 18, wherein the insoluble organic ethylene inhibitor comprises aminoisobutyric acid.

24. A method as claimed in claim 18, wherein the insoluble organic antibacterials comprises thiabendazole or tetrachloroisophthalonitrile.

25. A method as claimed in claim 21, wherein the thickener is xanthan gum.

26. A method as claimed in claim 21, wherein the polymer type dispersant comprises an alkylamine based nonionic surfactant.

27. A method as claimed in claim 26, wherein the alkylamine based nonionic surfactant is a polyoxyethylene alkylamine based surfactant.

28. A method as claimed in claim 21, wherein the ester based nonionic, surfactant comprises a polyoxyethylene hydrogenated castor oil triisostearate or a polyethylene glycol, diisostearate.

29. A method as claimed in claim 21, wherein the ether based nonionic surfactant is a polyoxyethylene hydrogenated castor oil.

30. A method as claimed in claim 21, wherein the ether based nonionic surfactant is a nonionic type polyoxyethylene alkylanine based surfactant.

31. A method as claimed in claim 18, wherein the composition further comprises a fluidizing agent and/or a dispersion stabilization agent and/or humectants.

32. A method as claimed in claim 31, wherein the fluidizing agent and/or the dispersion stabilization agent is selected from the group consisting of polyacrylamides.

33. A method as claimed in claim 31, wherein the humectants are selected from the group consisting of sorbitol, polyethylene glycol, 1,3-butylene glycol and concentrated glycerin.

34. A method as claimed in claim 21, wherein the ether based nonionic surfactant is polyoxyethylene hydrogenated castor oil.

\* \* \* \* \*